United States Patent
Stremmel

(12) 
(10) Patent No.: US 6,677,319 B1
(45) Date of Patent: Jan. 13, 2004

(54) PHOSPHATIDYLCHOLINE AS MEDICATION WITH PROTECTIVE EFFECT LARGE INTESTINAL MUCOSA

(76) Inventor: Wolfgang Stremmel, Heidelberg (DE)

( * ) Notice: Subject to any disclaimer, the term of this patent is extended or adjusted under 35 U.S.C. 154(b) by 0 days.

(21) Appl. No.: 09/762,195

(22) PCT Filed: Aug. 6, 1999

(86) PCT No.: PCT/DE99/02426

§ 371 (c)(1),
(2), (4) Date: Jul. 5, 2001

(87) PCT Pub. No.: WO00/07577

PCT Pub. Date: Feb. 17, 2000

(30) Foreign Application Priority Data

Aug. 6, 1998 (DE) .......................... 198 35 526
Dec. 15, 1998 (DE) .......................... 198 57 750

(51) Int. Cl.[7] ............................................. A01N 57/26
(52) U.S. Cl. .......................... 514/78; 554/80; 426/489
(58) Field of Search .............................. 584/80; 514/78; 424/489

(56) References Cited

FOREIGN PATENT DOCUMENTS

| JP | 61 047418 A | | 3/1986 |
|---|---|---|---|
| JP | 61-047418 | * | 3/1986 |
| WO | WO 95/18622 A1 | | 7/1995 |
| WO | WO 95/26646 A1 | | 10/1995 |
| WO | 95/26646 | * | 10/1995 |

OTHER PUBLICATIONS

Fabia et al., Digestion, vol. 53, No. 1–2, pp. 35–44, 1992.*
Mourelle et al., Gastroenterology, vol. 110, No. 4, pp. 1093–1097, 1996.*
*Effects of Phosphatidylcholine and Phosphatidylinsitol on Acetic–Acid–Induced Colitis in the Rat*, R. Fabia et al., Digestion, vol. 53, No. 1–2, 1992, pp. 35–44.
*Polyunsaturated Phosphatidylcholine Prevents Stricture Formation in a Rat Model of Colitis*, M. Mourelle et al., Gastroenterology, 1996, vol. 110, No. 4, 1996, pp. 1093–1097.
*The Human MDR3 P–Glycoprotein Promotes Translocation of Phosphatidylcholine Through the Plasma Membrane of Fibroblasts From Transgenic Mice*, A. J. Smith et al., FEBS Letters, 354, 1994, pp. 263–266.
*Mutations in the MDR3 Gene Cause Progressive Familial Intrahepatic Cholestasis*, J. M. L. De Vree et al., Pro. Natl. Acad. Sci. USA, vol. 95, Jan. 1998, pp. 282–287.
*MDRI P–Glycoprotein Is a Lipid Translocase of Broad Specificity, While MDR3 P–Glycoprotein Specifically Translocates Phosphatidylcholine*, A van Helvoort et al., Cell, vol. 87, Nov. 1996, pp. 507–517.
*A Novel Model of Inflammatory Bowel Disease: Mice Deficient for the Multiple Drug Resistance Gene, mdrla, Spontaneously Develop Colitis*, C. M. Panwala et al., The American Association of Immunologists, 1998, pp. 5733–5744.

* cited by examiner

Primary Examiner—Deborah D. Carr
(74) Attorney, Agent, or Firm—Alston & Bird LLP

(57) ABSTRACT

The presented invention relates to a medication containing a therapeutically effective amount of phosphatidylcholine as active substrate for treatment of disease where phosphatidylcholine has an advantageous, protective effect on the mucosa of large intestine. The invention also relates to the use and application form of phosphatidylcholine for local treatment of inflammation of the large intestine and prophylaxis against cancer of the colon. Phosphatidylcholine can be administered as a rectal installation for local treatment of inflammation (in rectum or pouch) as well as in orally administered delayed-release form. The orally administered, delayed-release form of phosphatidylcholine prevents absorption in upper intestine and thus provides targeted release in the lower sections of the small intestine or colon.

14 Claims, 6 Drawing Sheets upper line: MDR1
lower line: MDR3

Homology: 75,4 %

```
 51 actaaagtcggagtatcttcttccaagatttcacgtcttggtggccgttc 100
                                 | | | | |  |  ||||
  1 .............................cctgccagacacgcgcgaggttc  23

101 caaggagcgcgaggtcgggatggatcttgaaggggaccgcaatggaggag 150
     | |  | |  | || ·|| |   |    |  |||| |    ||·| |
 24 gaggctgagatggatcttgaggcggcaaagaacggaacagcctggcgccc  73
                          ━━━━━━━━━━━━━━━━━━▶
151 ca..aagaagaagaactttttaaactgaacaataaaagtgaaaagata   198
    || |    ||| |    ||| ||||| || | || ||·|| | |
 74 cacgagcgcggagggcgactttgaactgggcatcagcagcaaacaaaaaa 123

199 agaaggaaaagaaacc......aactgtcagtgtattttcaatgtttcgc 242
    |||  ||| |||  |        ||  | |  ||||||  ||·||||||
124 ggaaaaaaacgaagacagtgaaaatgattggagtattaacattgtttcga 173

243 tattcaaattggcttgacaagttgtatatggtggtgggaactttggctgc 292
    || ||  ||||||  || || |||| ||||  | |||| |  ||| ||
174 tactccgattggcaggataaattgtttatgtcgctgggtaccatcatggc 223
                                          ━━━━━━━━━━
293 catcatccatgggctggacttcctctcatgatgctggtgtttggagaaa  342
    |||    || ||   | || ||·|| ||||||||| ||·||||||||| |
224 catagctcacggatcaggtctcccctcatgatgatagtatttggagaga  273
    ━━━━━━━━━━▶
343 tgacagatatctttgcaaatgcagga.aatttagaagatctgatgtcaaa 391
    ||||·|| |  ||||    || | | |   | | | |    ||  || ||
274 tgactgacaaatttgttgatactgcaggaaacttctcctttccagtgaac 323

392 catcactaatagaagtgatatcaatgatacagggttcttcatgaatctgg 441
      |  ||   |   |  | ||| ||            || | |||||
324 ttttccttgtcgctgctaaatccagg............caaaattctgg  360

442 aggaagacatgaccaggtatgcctattattacagtggaattggtgctggg 491
    |·|||||·||||| ||||||| ||| ||| ||| |   ||| |·|||||||
361 aagaagaaatgactagatatgcatattactactcaggattgggtgctgga 410

492 gtgctggttgctgcttacattcaggtttcatttggtgcctggcagctgg  541
    || || ||||||||| || |· || ||·||||||||||||·|||||||||
411 gttcttgttgctgcctatatacaagtttcattttggactttggcagctgg 460

542 aagacaaatacacaaaattagaaaacagttttttcatgctataatgcgac 591
    |||| ||  |||||||| | |||||||||||||||||||·| | || ||
461 tcgacagatcaggaaaattaggcagaagttttttcatgctattctacgac 510
```

Fig. 1

```
 592 aggagataggctggtttgatgtgcacgatgttggggagcttaacacccga  641
     ||||  |||||  ||||||||  |  | ||     ||  || || || ||
 511 aggaaataggatggtttgacatcaatgacaccactgaactcaatacgcgg  560
                        ←━━━━━━━━━━━━━━━━━━━━━→

642 cttacagatgatgtctccaagattaatgaaggaattggtgacaaaattgg  691
     || |||||| ||      ||||||| || | ||||||||||||||  ||||
 561 ctaacagatgacatctccaaaatcagtgaaggaattggtgacaaggttgg  610

692 aatgttctttcagtcaatggcaacattttcactgggtttatagtaggat   741
     ||||||||||||  || | || || |||||  | || || ||||| ||||
 611 aatgttctttcaagcagtagccacgttttttgcaggattcatagtgggat  660

742 ttacacgtggttggaagctaacccttgtgattttggccatcagtcctgtt  791
     | |   | || ||||||||| |||||||||  |||||||||||| || ||
 661 tcatcagaggatggaagctcacccttgtgataatggccatcagccctatt  710

792 cttggactgtcagctgctgtctgggcaaagatactatcttcatttactga  841
     || ||||| || || || || |||||||||||||||||| |||||| |||
 711 ctaggactctctgcagccgtttgggcaaagatactctcggcatttagtga  760

842 taaagaactcttagcgtatgcaaaagctggagcagtagctgaagaggtct  891
     ||||||||   || ||||||||||||| || || || || |||||||
 761 caaagaactagctgcttatgcaaaagcaggcgccgtggcagaagaggctc  810

892 tggcagcaattagaactgtgattgcatttggaggacaaaagaaagaactt  941
     |||  ||·|| ||  ||||||||| || || || || ||  ||||| ||
 811 tgggggccatcaggactgtgatagctttcggggccagaacaaagagctg  860

942 gaaaggtacaacaaaaatttagaagaagctaaaagaattgggataaagaa  991
     ||||||||  |  ||| ||||||||  | ||  |||| ||| ||  |  ||
 861 gaaaggtatcagaaacatttagaaaatgccaaagagattggaattaaaaa  910

992 agctattacagccaatatttctataggtgctgctttcctgctgatctatg  1041
     |||||||  ||||  |||||  |||   |||  ||||||| |  || ||||
 911 agctatttcagcaaacatttccatgggtattgccttcctgttaatatatg  960

1042 catcttatgctctggccttctggtatgggaccaccttggtcctctcaggg  1091
     ||||  ||||||||||||||||||||||| ||||  | ·|||  |  |||
 961 catcatatgcactggccttctggtatggatccactctagtcatatcaaaa  1010

1092 gaatattctattggacaagtactcac...tgtatttctgtattaattgg   1138
     ||||||  |||||||| | | | ||      |  |||| |  ||||||||
1011 gaatatactattggaaatgcaatgacagttttttttcaatcctaattgg   1060

1139 ggcttttagtgttggacaggcatctccaagcattgaagcatttgcaaatg  1188
     |||||  |||||||| ||||  | ||  | ||| || ||||| |||||||
1061 agctttcagtgttggccaggctgccccatgtattgatgcttttgccaatg  1110

1189 caagaggagcagcttatgaaatcttcaagataattgataataagccaagt  1238
     ||||||||||||| ||||||  |||||| | || |||||||||||  | |
1111 caagaggagcagcatatgtgatctttgatattattgataataatcctaaa  1160

1239 attgacagctattcgaagagtgggcacaaaccagataatattaagggaaa  1288
     |||||||| |  ||  |||| || ||||||||||||| |  ||  || ||
1161 attgacagttttcagagagaggacacaaaccagacagcatcaaagggaa  1210
```

Fig. 1 (cont.)

```
1289 tttggaattcagaaatgttcacttcagttacccatctcgaaaagaagtta 1338
     |||||| ||||  |||||||||   ||||||  ||||||       | ||| |
1211 tttggagttcaatgatgttcactttcttacccttctcgagctaacgtca 1260

1339 agatcttgaagggtctgaacctgaaggtgcagagtgggcagacggtggcc 1388
     ||||||||||||| ||  |||||||||||||||||||||||||||||||
1261 agatcttgaagggcctcaacctgaaggtgcagagtgggcagacggtggcc 1310

1389 ctggttggaaacagtggctgtgggaagagcacaacagtccagctgatgca 1438
     |||||||||   |||||||||||||||||||||||   |||||||||| ||
1311 ctggttggaagtagtggctgtgggaagagcacaacggtccagctgataca 1360

1439 gaggctctatgaccccacagaggggatggtcagtgttgatggacaggata 1488
     ||||||||||||     ||||| |  | |   ||||||| ||||||||
1361 gaggctctatgaccctgatgagggcacaattaacattgatgggcaggata 1410

1489 ttaggaccataaatgtaaggtttctacgggaaatcattggtgtggtgagt 1538
     ||||||  |  || ||||||  |  |||  ||||||||||||||||||||
1411 ttaggaactttaatgtaaactatctgagggaaatcattggtgtggtgagt 1460

1539 caggaacctgtattgtttgccaccacgatagctgaaaacattcgctatgg 1588
     ||||| || ||  ||||| |||||||| |||||||||| ||| | |||||
1461 caggagccggtgctgttttccaccacaattgctgaaaatatttgttatgg 1510

1589 ccgtgaaaatgtcaccatggatgagattgagaaagctgtcaaggaagcca 1638
     |||||  |||||  |||||||||||||  |||||||||||||| ||||||
1511 ccgtggaaatgtaaccatggatgagataaagaaagctgtcaaagaggcca 1560

1639 atgcctatgactttatcatgaaactgcctcataaatttgacaccctggtt 1688
     | ||||||||  |||||||||||  |  ||  ||||||||||||||||||
1561 acgcctatgagtttatcatgaaattaccacagaaatttgacaccctggtt 1610

1689 ggagagagaggggcccagttgagtggtgggcagaagcagaggatcgccat 1738
     ||||||||||||||||||  ||||||||||||||||||||||||||||||
1611 ggagagagaggggcccagctgagtggtgggcagaagcagaggatcgccat 1660

1739 tgcacgtgccctggttcgcaacccaagatcctcctgctggatgaggcca 1788
     |||||||||||||||||||||||||||||||| ||||||||||||||||
1661 tgcacgtgccctggttcgcaacccaagatccttctgctggatgaggcca 1710

1789 cgtcagccttggacacagaaagcgaagcagtggttcaggtggctctggat 1838
     ||||||| ||||||||||||||| ||||| |||||   |||   ||||||
1711 cgtcagcattggacacagaaagtgaagctgaggtacaggcagctctggat 1760

1839 aaggccagaaaaggtcggaccaccattgtgatagctcatcgtttgtctac 1888
     |||||||||   |||| |||||||||||||||||| || || ||||||||
1761 aaggccagagaaggccggaccaccattgtgatagcacaccgactgtctac 1810

1889 agttcgtaatgctgacgtcatcgctggtttcgatgatggagtcattgtgg 1938
     |  ||  ||||| || |||||||||| || || ||||||||| || ||||
1811 ggtccgaaatgcagatgtcatcgctgggtttgaggatggagtaattgtgg 1860

1939 agaaaggaaatcatgatgaactcatgaaagagaaaggcatttacttcaaa 1988
     || ||||||  ||    ||||| |||||| ||||  || | ||||||||
1861 agcaaggaagccacagcgaactgatgaagaaggaagggtgtacttcaaa 1910
```

Fig. 1 (cont.)

```
1989 cttgtcacaatgcagacagcaggaaatgaagttgaattagaaaatgcagc 2038
     ||||||| ||||||||| |||||| | | | ||    ||
1911 cttgtcaacatgcagacatcaggaagccagatccagtcaga......aga 1954

2039 tgatgaatccaaaagtgaaattgatgccttggaaatgtcttcaaatgatt 2088
     ||||  ||  |||||  ||||   ||||  ||||   ||||| |
1955 atttgaactaaatgatgaaaaaggctgccactagaatggccccaaatggct 2004

2089 caagatccagtctaataagaaaaagatcaactcgtaggagtgtccgtgga 2138
     | ||| | ||| | ||  |     |     |    |  | |
2005 ggaaatctcgcctatttaggcattctactcagaaaaaccttaaaaattca 2054

2139 tcacaagcccaagacagaaagcttagtaccaaagaggctctggatgaaag 2188
     |     ||  | ||    |  || |  || || ||
2055 caaatgtgtcagaagagccttgatgtggaaaccgatggacttgaagcaaa 2104

2189 tataccTCCagtttccttttggaggattatgaagctaaatttaactgaat 2238
     | | || ||||| || | | |||| || ||| ||| ||||
2105 tgtgccaccagtgtcctttctgaaggtcctgaaactgaataaaacagaat 2154

2239 ggccttatttgttgttggtgtatttgtgccattataaatggaggcctg 2288
     |||| || |||||| || ||   | | ||||||||| |||||  || ||
2155 ggccctactttgtcgtgggaacagtatgtgccattgccaatgggggctt 2204

2289 caaccagcatttgcaataatattttcaaagattataggggttttacaag 2338
     || || |||||| | ||||| |||  |||| ||| |||| | |||||  |
2205 cagccggcatttttcagtcatattctcagagatcatagcgattttggacc 2254

2339 aattgatgatcctgaaacaaaacgacagaatagtaacttgttttcactat 2388
     |   |||||  || |   || |   ||||| ||| ||| ||  ||  |
2255 aggcgatga...tgcagtgaagcagcagaagtgcaacatattctctttga 2301

2389 tgtttctagcccttggaattatttcttttattacattttttccttcagggt 2438
     | || || || ||||||||||||||||| |||| || |||||||||||
2302 ttttcttatttctgggaattatttcttttttactttcttccttcagggt 2351

2439 ttcacatttggcaaagctggagagatcctcaccaagcggctccgatacat 2488
     ||||| ||||| ||||||||| |||||||||||| ||   |  ||
2352 ttcacgtttgggaaagctggcgagatcctcaccagaagactgcggtcaat 2401

2489 ggttttccgatccatgctcagacaggatgtgagttggtttgatgaccta 2538
     ||  |||   | | ||||||| ||||||| ||||| ||||||| |||||||| ||
2402 ggcttttaaagcaatgctaagacaggacatgagctggtttgatgaccata 2451

2539 aaaacaccactggagcattgactaccaggctcgccaatgatgctgctcaa 2588
     ||||||  ||||| ||| | ||  ||||  || || |||| |||||||
2452 aaaacagtactggtgcactttctacaagacttgccacagatgctgcccaa 2501

2589 gttaaaggggctataggttccaggcttgctgtaattacccagaatatagc 2638
     ||  |||| || | |||   ||||| | ||| ||||||||||||||||
2502 gtccaaggagccacaggaaccaggttggctttaattgcacagaatatagc 2551

2639 aaatcttgggacaggaataattatatccttcatctatggttggcaactaa 2688
     || |||||| || || || || || |||||| |||||||||||  |||
2552 taaccttggaactggtattatcatatcatttatctacggttggcagttaa 2601
```

Fig. 1 (cont.)

```
2689 cactgttactcttagcaattgtacccatcattgcaatagcaggagttgtt 2738
     | || || || |||||| |||| ||.|| ||||| |  ||||| |||||
2602 ccctattgctattagcagttgttccaattattgctgtgtcaggaattgtt 2651

2739 gaaatgaaaatgttgtctggacaagcactgaaagataagaaagaactaga 2788
     ||||||||| ||||| |||||  | ||     | ||||||| |||||||| ||
2652 gaaatgaaattgttggctggaaatgccaaaagagataaaaaagaactgga 2701

2789 aggtgctgggaagatcgctactgaagcaatagaaaacttccgaaccgttg 2838
     || |||||| ||||| || || || |||||||||| |  | || ||||
2702 agctgctggaaagattgcaacagaggcaatagaaaatattaggacagttg 2751
            ←————————————————→

2839 tttctttgactcaggagcagaagtttgaacatatgtatgctcagagtttg 2888
     | |||||||  |||||    || |||||||     |||||| |||  |||
2752 tgtctttgacccaggaaagaaaatttgaatcaatgtatgttgaaaaattg 2801

2889 caggtaccatacagaaactctttgaggaaagcacacatctttggaattac 2938
     | | ||| ||||| || ||| ||   ||| |||||||||| ||||||||
2802 tatggaccttacaggaattctgtgcagaaggcacacatctatggaattac 2851

2939 attttccttcacccaggcaatgatgtattttctatgctggatgtttcc 2988
     |||    || | || ||| |  ||||||||||||||||| || ||||| |
2852 ttttagtatctcacaagcatttatgtattttcctatgccggttgttttc 2901

2989 ggtttggagcctacttggtggcacataaactcatgagctttgaggatgtt 3038
     | |||||  || || |  |  ||  ||| |||| |||||||
2902 gatttggtgcatatctcattgtgaatggacatatgcgcttcagagatgtt 2951

3039 ctgttagtattttcagctgttgtctttggtgccatggccgtggggcaagt 3088
     |  | || |||||| ||||  |||| ||||||| |  | ||  | |
2952 attctggtgttttctgcaattgtatttggtgcagtggctctaggacatgc 3001

3089 cagttcatttgctcctgactatgccaaagccaaaatatcagcagcccaca 3138
     ||||||||||||| |||||||||| |||||| |  | || ||||||||||
3002 cagttcatttgctccagactatgctaaagctaagctgtctgcagcccact 3051

3139 tcatcatgatcattgaaaaaacccctttgattgacagctacagcacggaa 3188
     |  ||||| | ||||| |   ||| |||||||||||||||||  ||
3052 tattcatgctgtttgaaagacaacctctgattgacagctacagtgaagag 3101
                                            ←————————

3189 ggcctaatgccgaacacattggaaggaaatgtcacatttggtgaagttgt 3238
     || || | |||  | | ||| ||||||||| ||||||| ||||| ||
3102 gggctgaagcctgataaatttgaaggaaatataacatttaatgaagtcgt 3151
     ————————————————→                          ←————

3239 attcaactatcccacccgaccggacatcccagtgcttcagggactgagcc 3288
     ||||||||||||||||| |  || | ||||||||||||||| |||||||
3152 gttcaactatcccacccgagcaaacgtgccagtgcttcaggggctgagcc 3201

3289 tggaggtgaagaagggccagacgctggctctggtgggcagcagtggctgt 3338
     |||||||||||||||| ||||| |||  || ||||||||||||||||||
3202 tggaggtgaagaaaggccagacactagccctggtgggcagcagtggctgt 3251

3339 gggaagagcacagtggtccagctcctggagcggttctacgacccccttggc 3388
     |||||||||||| |||||||||||||||||||||||||||||||||||||
3252 gggaagagcacggtggtccagctcctggagcggttctacgacccccttggc 3301
```

Fig. 1 (cont.)

```
3389 agggaaagtgctgcttgatggcaaagaaataaagcgactgaatgttcagt 3438
     ||||  ||||||  ||  |||||  |||||  ||||  |||  |||||  ||||
3302 ggggacagtgcttctcgatggtcaagaagcaaagaaactcaatgtccagt 3351

3439 ggctccgagcacacctgggcatcgtgtcccaggagcccatcctgtttgac 3488
     |||||  ||||  ||  ||  ||  ||||||||  ||||||||  |||||  ||||||
3352 ggctcagagctcaactcggaatcgtgtctcaggagcctatcctatttgac 3401

3489 tgcagcattgctgagaacattgcctatggagacaacagccgggtggtgtc 3538
     ||||||||||  |||||  ||||||||||||||||||||||||||||||  ||  ||
3402 tgcagcattgccgagaatattgcctatggagacaacagccgggttgtatc 3451

3539 acaggaagagattgtgagggcagcaaaggaggccaacatacatgccttca 3588
     ||||||  ||  |||||||||  |||||  ||  |  ||||||||||||  |  ||||
3452 acaggatgaaattgtgagtgcagccaaagctgccaacatacatcctttca 3501

3589 tcgagtcactgcctaataaatatagcactaaagtaggagacaaaggaact 3638
     ||||| |  |  ||  |  ||||||  ||  | |||  |||||  ||  ||  |||
3502 tcgagacgttacccacaaatatgaaacaagagtgggagataagggact 3551

3639 cagctctctggtggccagaaacaacgcattgccatagctcgtgcccttgt 3688
     |||||||  ||  ||  ||  |||||  |  |||||  ||  ||  ||  |||||  |
3552 cagctctcaggaggtcaaaaacagaggattgctattgccgagccctcat 3601

3689 tagacagcctcatatttgcttttggatgaagccacgtcagctctggata 3738
     |||||  |||||  ||  |  ||  ||||||||||  ||  ||||||||||||
3602 cagacaacctcaaatcctcctgttggatgaagctacatcagctctggata 3651

3739 cagaaagtgaaaaggttgtccaagaagccctggacaaagccagagaaggc 3788
     |  |||||||||||||||||||||||||||||||||||||||||||||||
3652 ctgaaagtgaaaaggttgtccaagaagccctggacaaagccagagaaggc 3701

3789 cgcacctgcattgtgattgctcaccgcctgtccaccatccagaatgcaga 3838
     ||||||||||||||||||||||||||||||||||||||||||||||||||
3702 cgcacctgcattgtgattgctcaccgcctgtccaccatccagaatgcaga 3751

3839 cttaatagtggtgtttcagaatggcagagtcaaggagcatggcacgcatc 3888
     |||||||||||||||||||||||| ||||||||||||||||||||||||
3752 cttaatagtggtgtttcagaatgggagagtcaaggagcatggcacgcatc 3801

3889 agcagctgctggcacagaaaggcatctattttcaatggtcagtgtccag 3938
     |||||||||||||||||||||||||||||||||||||||||||||||||
3802 agcagctgctggcacagaaaggcatctattttcaatggtcagtgtccag 3851

3939 gctggaacaaagcgccagtgaactctgactgtatgagatgttaaatactt 3988
     |||||  |||  ||  |    ||||||  |  ||  |  |  ||  |||||  |
3852 gctgggacacagaacttatgaactttgctacagtatatttaaaaataa 3901

3989 tttaatatttgtttagatatgacatttattcaaagttaaaagcaaacact 4038
     ||  |  |||  |  ||     ||
3902 attcaaattattctacccattttt...................... 3924
```

Fig. 1 (cont.)

SEQUENCE LISTING

<160> NUMBER OF SEQ ID NOS: 23

<210> SEQ ID NO 1
<211> LENGTH: 3988
<212> TYPE: DNA
<213> ORGANISM: Homo sapiens

<400> SEQUENCE: 1

```
actaaagtcg gagtatcttc ttccaagatt tcacgtcttg gtggccgttc caaggagcgc      60
gaggtcggga tggatcttga aggggaccgc aatggaggag caagaagaa gaactttttt     120
aaactgaaca ataaaagtga aaagataag aaggaaaaga aaccaactgt cagtgtattt     180
tcaatgtttc gctattcaaa ttggcttgac aagttgtata tggtggtggg aactttggct     240
gccatcatcc atggggctgg acttcctctc atgatgctgg tgtttggaga atgacagat     300
atctttgcaa atgcaggaaa tttagaagat ctgatgtcaa acatcactaa tagaagtgat     360
atcaatgata cagggttctt catgaatctg gaggaagaca tgaccaggta tgcctattat     420
tacagtggaa ttggtgctgg ggtgctggtt gctgcttaca ttcaggtttc attttggtgc     480
ctggcagctg gaagacaaat acacaaaatt agaaaacagt ttttttcatgc tataatgcga     540
caggagatag gctggtttga tgtgcacgat gttggggagc ttaacacccg acttacagat     600
gatgtctcca agattaatga aggaattggt gacaaaattg gaatgttctt tcagtcaatg     660
gcaacatttt tcactgggtt tatagtagga tttacacgtg gttggaagct aaccccttgtg     720
attttggcca tcagtcctgt tcttggactg tcagctgctg tctgggcaaa gatactatct     780
tcatttactg ataagaaact cttagcgtat gcaaaagctg gagcagtagc tgaagaggtc     840
ttggcagcaa ttagaactgt gattgcattt ggaggacaaa agaaagaact tgaaaggtac     900
aacaaaaatt tagaagaagc taaaagaatt gggataaaga aagctattac agccaatatt     960
tctataggtg ctgctttcct gctgatctat gcatcttatg ctctggcctt ctggtatggg    1020
accaccttgg tcctctcagg ggaatattct attggacaag tactcactgt attttctgta    1080
ttaattgggg cttttagtgt tggacaggca tctccaagca ttgaagcatt tgcaaatgca    1140
agaggagcag cttatgaaat cttcaagata attgataata agccaagtat tgacagctat    1200
tcgaagagtg ggcacaaacc agataatatt aagggaaatt tggaattcag aaatgttcac    1260
ttcagttacc catctcgaaa agaagttaag atcttgaagg gtctgaacct gaaggtgcag    1320
agtgggcaga cggtggccct ggttggaaac agtggctgtg ggaagagcac aacagtccag    1380
ctgatgcaga ggctctatga ccccacagag gggatggtca gtgttgatgg acaggatatt    1440
aggaccataa atgtaaggtt tctacgggaa atcattggtg tggtgagtca ggaacctgta    1500
ttgtttgcca ccacgatagc tgaaaacatt cgctatggcc gtgaaaatgt caccatggat    1560
gagattgaga aagctgtcaa ggaagccaat gcctatgact ttatcatgaa actgcctcat    1620
aaatttgaca ccctggttgg agagagaggg gcccagttga gtggtgggca gaagcagagg    1680
atcgccattg cacgtgccct ggttcgcaac cccaagatcc tcctgctgga tgaggccacg    1740
tcagccttgg acacagaaag cgaagcagtg gttcaggtgg ctctggataa ggccagaaaa    1800
ggtcggacca ccattgtgat agctcatcgt ttgtctacag ttcgtaatgc tgacgtcatc    1860
gctggtttcg atgatggagt cattgtggag aaaggaaatc atgatgaact catgaaagag    1920
aaaggcattt acttcaaact tgtcacaatg cagacagcag gaaatgaagt tgaattagaa    1980
aatgcagctg atgaatccaa aagtgaaatt gatgccttgg aaatgtcttc aaatgattca    2040
agatccagtc taataagaaa aagatcaact cgtaggagtg tccgtggatc acaagcccaa    2100
gacagaaagc ttagtaccaa agaggctctg gatgaaagta tacctccagt ttccttttgg    2160
aggattatga agctaaattt aactgaatgg ccttattttg ttgttggtgt attttgtgcc    2220
attataaatg gaggcctgca accagcattt gcaataatat tttcaaagat tataggggtt    2280
```

-continued

| | |
|---|---|
| tttacaagaa ttgatgatcc tgaaacaaaa cgacagaata gtaacttgtt ttcactattg | 2340 |
| tttctagccc ttggaattat ttcttttatt acattttcc ttcagggttt cacatttggc | 2400 |
| aaagctggag agatcctcac caagcggctc cgatacatgg ttttccgatc catgctcaga | 2460 |
| caggatgtga gttggtttga tgaccctaaa acaccactg gagcattgac taccaggctc | 2520 |
| gccaatgatg ctgctcaagt taaggggct ataggttcca ggcttgctgt aattacccag | 2580 |
| aatatagcaa atcttgggac aggaataatt atatccttca tctatggttg caactaaca | 2640 |
| ctgttactct tagcaattgt acccatcatt gcaatagcag gagttgttga aatgaaaatg | 2700 |
| ttgtctggac aagcactgaa agataagaaa gaactagaag gtgctgggaa gatcgctact | 2760 |
| gaagcaatag aaaacttccg aaccgttgtt tctttgactc aggagcagaa gtttgaacat | 2820 |
| atgtatgctc agagtttgca ggtaccatac agaaactctt tgaggaaagc acacatcttt | 2880 |
| ggaattacat tttccttcac ccaggcaatg atgtattttt cctatgctgg atgtttccgg | 2940 |
| tttggagcct acttggtggc acataaactc atgagctttg aggatgttct gttagtattt | 3000 |
| tcagctgttg tctttggtgc catggccgtg gggcaagtca gttcatttgc tcctgactat | 3060 |
| gccaaagcca aaatatcagc agcccacatc atcatgatca ttgaaaaaac ccctttgatt | 3120 |
| gacagctaca gcacggaagg cctaatgccg aacacattgg aaggaaatgt cacatttggt | 3180 |
| gaagttgtat tcaactatcc caccogaccg gacatcccag tgcttcaggg actgagcctg | 3240 |
| gaggtgaaga agggccagac gctggctctg gtgggcagca gtggctgtgg gaagagcaca | 3300 |
| gtggtccagc tcctggagcg gttctacgac cccttggcag ggaaagtgct gcttgatggc | 3360 |
| aaagaaataa agcgactgaa tgttcagtgg ctccgagcac acctgggcat cgtgtcccag | 3420 |
| gagcccatcc tgtttgactg cagcattgct gagaacattg cctatggaga caacagccgg | 3480 |
| gtggtgtcac aggaagagat tgtgagggca gcaaggagg ccaacataca tgccttcatc | 3540 |
| gagtcactgc ctaataaata tagcactaaa gtaggagaca aggaactca gctctctggt | 3600 |
| ggccagaaac aacgcattgc catagctcgt gcccttgtta dacagcctca tattttgctt | 3660 |
| ttggatgaag ccacgtcagc tctggataca gaaagtgaaa aggttgtcca agaagccctg | 3720 |
| gacaaagcca gagaaggccg cacctgcatt gtgattgctc accgcctgtc caccatccag | 3780 |
| aatgcagact aatagtggt gtttcagaat ggcagagtca aggagcatgg cacgcatcag | 3840 |
| cagctgctgg cacagaaagg catctatttt tcaatggtca gtgtccaggc tggaacaaag | 3900 |
| cgccagtgaa ctctgactgt atgagatgtt aaatactttt taatatttgt ttagatatga | 3960 |
| catttattca aagttaaaag caaacact | 3988 |

<210> SEQ ID NO 2
<211> LENGTH: 3924
<212> TYPE: DNA
<213> ORGANISM: Homo sapiens

<400> SEQUENCE: 2

| | |
|---|---|
| cctgccagac acgcgcgagg ttcgaggctg agatggatct tgaggcggca aagaacggaa | 60 |
| cagcctggcg ccccacgagc gcggagggcg actttgaact gggcatcagc agcaaacaaa | 120 |
| aaaggaaaaa aacgaagaca gtgaaaatga ttggagtatt aacattgttt cgatactccg | 180 |
| attggcagga taaattgttt atgtcgctgg gtaccatcat ggccatagct cacggatcag | 240 |
| gtctcccct catgatgata gtatttggag agatgactga caatttgtt gatactgcag | 300 |
| gaaacttctc cttccagtg aacttttcct tgtcgctgct aaatccaggc aaaattctgg | 360 |
| aagaagaaat gactagatat gcatattact actcaggatt gggtgctgga gttcttgttg | 420 |

-continued

```
ctgcctatat acaagtttca ttttggactt tggcagctgg tcgacagatc aggaaaatta      480
ggcagaagtt ttttcatgct attctacgac aggaaatagg atggtttgac atcaatgaca      540
ccactgaact caatacgcgg ctaacagatg acatctccaa aatcagtgaa ggaattggtg      600
acaaggttgg aatgttcttt caagcagtag ccacgttttt tgcaggattc atagtgggat      660
tcatcagagg atggaagctc acccttgtga taatggccat cagccctatt ctaggactct      720
ctgcagccgt ttgggcaaag atactctcgg catttagtga caaagaacta gctgcttatg      780
caaaagcagg cgccgtggca gaagaggctc tgggggccat caggactgtg atagctttcg      840
ggggccagaa caaagagctg aaaggtatc agaaacattt agaaaatgcc aaagagattg       900
gaattaaaaa agctatttca gcaaacattt ccatgggtat tgccttcctg ttaatatatg      960
catcatatgc actggccttc tggtatggat ccactctagt catatcaaaa gaatatacta     1020
ttggaaatgc aatgacagtt ttttttttcaa tcctaattgg agctttcagt gttggccagg     1080
ctgccccatg tattgatgct tttgccaatg caagaggagc agcatatgtg atctttgata     1140
ttattgataa taatcctaaa attgacagtt tttcagagag aggacacaaa ccagacagca     1200
tcaaagggaa tttggagttc aatgatgttc acttttctta cccttctcga gctaacgtca     1260
agatcttgaa gggcctcaac ctgaaggtgc agagtgggca gacggtggcc tggttggaa      1320 gtagtggctg tgggaagagc acaacggtcc agctgataca gaggctctat gaccctgatg     1380
agggcacaat taacattgat gggcaggata ttaggaactt taatgtaaac tatctgaggg     1440
aaatcattgg tgtggtgagt caggagccgg tgctgttttc caccacaatt gctgaaaata     1500
tttgttatgc ccgtggaaat gtaaccatgg atgagataaa gaaagctgtc aaagaggcca     1560
acgcctatga gtttatcatg aaattaccac agaaatttga caccctggtt ggagagagag     1620
gggcccagct gagtggtggg cagaagcaga ggatcgccat tgcacgtgcc ctggttcgca     1680
accccaagat ccttctgctg gatgaggcca cgtcagcatt ggacacagaa agtgaagctg     1740
aggtacaggc agctctggat aaggccgag aaggccggac caccattgtg atagcacacc      1800
gactgtctac ggtccgaaat gcagatgtca tcgctgggtt tgaggatgga gtaattgtgg     1860
agcaaggaag ccacagcgaa ctgatgaaga aggaagggt gtacttcaaa cttgtcaaca      1920
tgcagacatc aggaagccag atccagtcag aagaatttga actaaatgat gaaaaggctg     1980
ccactagaat ggccccaaat ggctggaaat ctcgcctatt taggcattct actcagaaaa     2040
accttaaaaa ttcacaaatg tgtcagaaga gccttgatgt ggaaaccgat ggacttgaag     2100
caaatgtgcc accagtgtcc tttctgaagg tcctgaaact gaataaaaca gaatggccct     2160
actttgtcgt gggaacagta tgtgccattg ccaatggggg gcttcagccg gcattttcag     2220
tcatattctc agagatcata gcgattttg gaccaggcga tgatgcagtg aagcagcaga     2280
agtgcaacat attctctttg attttcttat ttctgggaat tatttctttt tttacttttct     2340 tccttcaggg tttcacgttt gggaaagctg gcgagatcct caccagaaga ctgcggtcaa     2400
tggcttttaa agcaatgcta agacaggaca tgagctggtt tgatgaccat aaaaacagta     2460
ctggtgcact ttctacaaga cttgccacag atgctgccca agtccaagga gccacaggaa     2520
ccaggttggc tttaattgca cagaatatag ctaaccttgg aactggtatt atcatatcat     2580
ttatctacgg ttggcagtta accctattgc tattagcagt tgttccaatt attgctgtgt     2640
caggaattgt tgaaatgaaa ttgttggctg gaaatgccaa aagagataaa aaagaactgg     2700
aagctgctgg aaagattgca acagaggcaa tagaaaatat taggacagtt gtgtctttga     2760
```

-continued

| | |
|---|---|
| cccaggaaag aaaatttgaa tcaatgtatg ttgaaaaatt gtatggacct tacaggaatt | 2820 |
| ctgtgcagaa ggcacacatc tatggaatta cttttagtat ctcacaagca tttatgtatt | 2880 |
| tttcctatgc cggttgtttt cgatttggtg catatctcat tgtgaatgga catatgcgct | 2940 |
| tcagagatgt tattctggtg ttttctgcaa ttgtatttgg tgcagtggct ctaggacatg | 3000 |
| ccagttcatt tgctccagac tatgctaaag ctaagctgtc tgcagcccac ttattcatgc | 3060 |
| tgtttgaaag acaacctctg attgacagct acagtgaaga ggggctgaag cctgataaat | 3120 |
| ttgaaggaaa ataacatttt aatgaagtcg tgttcaacta tcccacccga gcaaacgtgc | 3180 |
| cagtgcttca ggggctgagc ctggaggtga agaaaggcca gacactagcc ctggtgggca | 3240 |
| gcagtggctg tgggaagagc acggtggtcc agctcctgga gcggttctac gaccccttgg | 3300 |
| cggggacagt gcttctcgat ggtcaagaag caaagaaact caatgtccag tggctcagag | 3360 |
| ctcaactcgg aatcgtgtct caggagccta tcctatttga ctgcagcatt gccgagaata | 3420 |
| ttgcctatgg agacaacagc cgggttgtat cacaggatga aattgtgagt gcagccaaag | 3480 |
| ctgccaacat acatccttc atcgagacgt taccccacaa atatgaaaca agagtgggag | 3540 |
| ataaggggac tcagctctca ggaggtcaaa acagaggat tgctattgcc cgagccctca | 3600 |
| tcagacaacc tcaaatcctc ctgttggatg aagctacatc agctctggat actgaaagtg | 3660 |
| aaaaggttgt ccaagaagcc ctggacaaag ccagagaagg ccgcacctgc attgtgattg | 3720 |
| ctcaccgcct gtccaccatc cagaatgcag acttaatagt ggtgtttcag aatgggagag | 3780 |
| tcaaggagca tggcacgcat cagcagctgc tggcacagaa aggcatctat ttttcaatgg | 3840 |
| tcagtgtcca ggctgggaca cagaacttat gaacttttgc tacagtatat tttaaaaata | 3900 |
| aattcaaatt attctaccca tttt | 3924 |

<210> SEQ ID NO 3
<211> LENGTH: 20
<212> TYPE: DNA
<213> ORGANISM: Artificial Sequence
<220> FEATURE:
<223> OTHER INFORMATION: forward primer

<400> SEQUENCE: 3
gcaaagaacg gaacagcctg                                                 20

<210> SEQ ID NO 4
<211> LENGTH: 21
<212> TYPE: DNA
<213> ORGANISM: Artificial Sequence
<220> FEATURE:
<223> OTHER INFORMATION: forward primer

<400> SEQUENCE: 4
ccatcatggc catagctcac g                                               21

<210> SEQ ID NO 5
<211> LENGTH: 20
<212> TYPE: DNA
<213> ORGANISM: Artificial Sequence
<220> FEATURE:
<223> OTHER INFORMATION: forward primer

<400> SEQUENCE: 5
catcaatgac accactgaac                                                 20

<210> SEQ ID NO 6
<211> LENGTH: 20

```
<212> TYPE: DNA
<213> ORGANISM: Artificial Sequence
<220> FEATURE:
<223> OTHER INFORMATION: forward primer

<400> SEQUENCE: 6
acccttctcg agctaacgtc                                              20

<210> SEQ ID NO 7
<211> LENGTH: 20
<212> TYPE: DNA
<213> ORGANISM: Artificial Sequence
<220> FEATURE:
<223> OTHER INFORMATION: forward primer

<400> SEQUENCE: 7
ctgatgaggg cacaattaac                                              20

<210> SEQ ID NO 8
<211> LENGTH: 21
<212> TYPE: DNA
<213> ORGANISM: Artificial Sequence
<220> FEATURE:
<223> OTHER INFORMATION: forward primer

<400> SEQUENCE: 8
caggaagcca gatccagtca g                                            21

<210> SEQ ID NO 9
<211> LENGTH: 20
<212> TYPE: DNA
<213> ORGANISM: Artificial Sequence
<220> FEATURE:
<223> OTHER INFORMATION: forward primer

<400> SEQUENCE: 9
aaaggctgcc actagaatgg                                              20

<210> SEQ ID NO 10
<211> LENGTH: 23
<212> TYPE: DNA
<213> ORGANISM: Artificial Sequence
<220> FEATURE:
<223> OTHER INFORMATION: forward primer

<400> SEQUENCE: 10
gtgtcagaag agccttgatg tgg                                          23

<210> SEQ ID NO 11
<211> LENGTH: 25
<212> TYPE: DNA
<213> ORGANISM: Artificial Sequence
<220> FEATURE:
<223> OTHER INFORMATION: forward primer

<400> SEQUENCE: 11
agcaatgcta agacaggaca tgagc                                        25

<210> SEQ ID NO 12
<211> LENGTH: 20
<212> TYPE: DNA
<213> ORGANISM: Artificial Sequence
<220> FEATURE:
<223> OTHER INFORMATION: forward primer

<400> SEQUENCE: 12
```

-continued ggaaagattg caacagaggc                                            20

<210> SEQ ID NO 13
<211> LENGTH: 21
<212> TYPE: DNA
<213> ORGANISM: Artificial Sequence
<220> FEATURE:
<223> OTHER INFORMATION: forward primer

<400> SEQUENCE: 13
gtgaagaggg gctgaagcct g                                          21

<210> SEQ ID NO 14
<211> LENGTH: 20
<212> TYPE: DNA
<213> ORGANISM: Artificial Sequence
<220> FEATURE:
<223> OTHER INFORMATION: reverse primer

<400> SEQUENCE: 14
gttcagtggt gtcattgatg                                            20

<210> SEQ ID NO 15
<211> LENGTH: 20
<212> TYPE: DNA
<213> ORGANISM: Artificial Sequence
<220> FEATURE:
<223> OTHER INFORMATION: reverse primer

<400> SEQUENCE: 15
gacgttagct cgagaagggt                                            20

<210> SEQ ID NO 16
<211> LENGTH: 20
<212> TYPE: DNA
<213> ORGANISM: Artificial Sequence
<220> FEATURE:
<223> OTHER INFORMATION: reverse primer

<400> SEQUENCE: 16
gttaattgtg ccctcatcag                                            20

<210> SEQ ID NO 17
<211> LENGTH: 21
<212> TYPE: DNA
<213> ORGANISM: Artificial Sequence
<220> FEATURE:
<223> OTHER INFORMATION: reverse primer

<400> SEQUENCE: 17
ctgactggat ctggcttcct g                                          21

<210> SEQ ID NO 18
<211> LENGTH: 20
<212> TYPE: DNA
<213> ORGANISM: Artificial Sequence
<220> FEATURE:
<223> OTHER INFORMATION: reverse primer

<400> SEQUENCE: 18
ccattctagt ggcagccttt                                            20

<210> SEQ ID NO 19
<211> LENGTH: 23
<212> TYPE: DNA
<213> ORGANISM: Artificial Sequence

```
<220> FEATURE:
<223> OTHER INFORMATION: reverse primer

<400> SEQUENCE: 19
ccacatcaag gctcttctga cac                                              23

<210> SEQ ID NO 20
<211> LENGTH: 20
<212> TYPE: DNA
<213> ORGANISM: Artificial Sequence
<220> FEATURE:
<223> OTHER INFORMATION: reverse primer

<400> SEQUENCE: 20
gcctctgttg caatctttcc                                                  20

<210> SEQ ID NO 21
<211> LENGTH: 21
<212> TYPE: DNA
<213> ORGANISM: Artificial Sequence
<220> FEATURE:
<223> OTHER INFORMATION: reverse primer

<400> SEQUENCE: 21
caggcttcag cccctcttca c                                                21

<210> SEQ ID NO 22
<211> LENGTH: 22
<212> TYPE: DNA
<213> ORGANISM: Artificial Sequence
<220> FEATURE:
<223> OTHER INFORMATION: reverse primer

<400> SEQUENCE: 22
tcgggtggga tagttgaaca cg                                               22

<210> SEQ ID NO 23
<211> LENGTH: 23
<212> TYPE: DNA
<213> ORGANISM: Artificial Sequence
<220> FEATURE:
<223> OTHER INFORMATION: reverse primer

<400> SEQUENCE: 23
gggctcgggc aatagcaatc ctc                                              23
```

PHOSPHATIDYLCHOLINE AS MEDICATION WITH PROTECTIVE EFFECT LARGE INTESTINAL MUCOSA

This application is a 371 of PCT/DE99/02426 filed Aug. 6, 1999.

The presented invention relates to medications containing as effective substrate phosphatidylcholine in an amount sufficient to treat diseases in which the mucosa-protective effect of phosphatidylcholine in colon and terminal ileum (including pouch mucosa) is of advantage. The medications are suitable for treatment of ulcerative colitis, pouchitis, other inflammatory diseases of colonic mucosa (Crohn's disease; diversion colitis; infectious enteritis/colitis; mucosal inflammation by irradiation, antibiotics, chemotherapeutic or pharmaceutical agents, chemicals) as well as for prophylaxis of colon cancer.

Chronic inflammatory bowel diseases, ulcerative colitis and Crohn's disease, affect in high degree young and medium-age adults with increasing frequency (prevalence of both diseases 1–2%). A chronic course with acute inflammatory episodes and numerous complications (development of fistulae and abscesses, stenoses, acute inflammations, bleedings, functional impairment of colonic mucosa, extraintestinal manifestations) characterize the natural course of these diseases. In particular, it is emphasized that ulcerative colitis after long-term course is associated with an increased risk to develop colonic cancer. Despite intensive research, the pathogenesis of these diseases could not be determined until today. Therefore only a symptomatic therapy is available which is not directed towards the cause of the disorder and often does not provide the desired success.

Between ulcerative colitis and Crohn's disease exist major differences, such that one can assume 2 different pathogenetic mechanisms. Crohn's disease can principally affect the entire gastrointestinal tract (main localization at the end of small intestine in terminal ileum). Inflammatory changes are localized circumscriptively in an otherwise healthy mucosa and can change with time. Main complications are inflammatory stenoses of intestinal segments as well as development of fistulae or abscesses. Manifestations outside the gastrointestinal tract are possible. Ulcerative colitis, in contrast, reveals a continuous inflammation with superficial ulceration starting at the end of the colon (proctum, rectum). According to severity of inflammation the colitis can spread upwards and finally the total colon can be affected. In high percentage also the end of the small intestine can be affected ("backwash ileitis"). Main complications are functional impairments of colonic mucosa associated with frequent diarrhea, bleedings of mucosal ulcerations and rarely dramatic inflammation of the entire mucosal wall (toxic megacolon). Frightening is the frequent development of colonic cancer after long-term course of the disease. Between both chronic inflammatory bowel diseases, an overlap of symptoms can be observed such that discrimination is often very difficult. Beside the often-insufficient symptomatic therapy in ulcerative colitis it is frequently necessary to remove the entire colon because of a complicated, severe clinical manifestation or the threatening danger of carcinoma development. This procedure includes construction of a reservoir (pouch) out of the last ileal loop, its positioning into the anal channel, fixation in this position and connection to the natural anus (after removal the rectal mucosa). This allows creation of a new reservoir for intestinal contents with the advantage to maintain the natural outlet (continence maintaining ileo-anal pouch construction). In about 30% of patients with ulcerative colitis the pouch can get inflamed (pouchitis) and can lead to significant complaints. When such a pouch construction is performed in other underlying diseases (e.g. familial adenomatous polyposis) only in exceptional cases inflammation develops.

WO 95/18622 describes the use of derivatives of 2-hydroxy-5-phenylazobencoic acid as chemoprotective substance for treatment of diseases of the colon.

It was the task of the present invention to provide additional medications for treatment of bowel diseases. Of surprise was the observation that phosphatidylcholine functions as mucosa protective substance. Like a protective layer phosphatidylcholine covers the mucosal cells and is therefore suitable as therapeutic substance for treatment of ulcerative colitis, pouchitis, other inflammatory bowel diseases (Crohn's disease, diversion colitis, infectious enteritis/colitis, inflammation due to irradiation, antibiotics, chemotherapeutic agents, pharmaca or chemicals) or for prophylaxis of colonic cancer.

Phosphatidylcholine (PC) (synonymously also the term lecithin is used) is a compound phosphorous containing lipid (phospholipid) with following schematic structural formula:

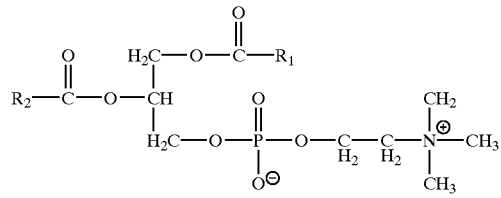

where $R_1$=a saturated or unsaturated fatty acid with 14–22 carbon atoms, and $R_2$=a saturated or unsaturated fatty acid with 14–22 carbon atoms.

For treatment of ulcerative colitis, pouchitis and the other above mentioned bowel inflammations oral preparations of phosphatidylcholine are suitable with specific or delayed substrate release in lower ileum and colon and/or rectal forms of application, e.g. as clysmas, suppositories or foam. For prophylaxis of colonic cancer, particularly in association with ulcerative colitis, oral application is preferred. Oral applications can be provided in form of suitable preparations, e.g. as tablets or capsules which prevent absorption from the first two thirds of the small intestine and lead to specific release in the lower part of the ileum.

Medications containing phosphatidylcholine can be provided locally as rectal applications (e.g. suppositories, foam or clysmas) or orally. The application of phosphatidylcholine occurs in lower ileum sections and colon, mainly to protect the colon mucosa against bacterial infection. For oral application such medications are particularly suitable which release the effective substrate in a delayed fashion (retarded preparations). This retardation of effective substrate release is most usefully achieved by covershields and/or carrier matrices which are gastric acid resistant and release the effective substrate in pH-dependent fashion into the lower ileum or colon. From a technical point of view, film covershields are suitable which contain as an example Eudragit®-acrylpolymers for directed release of the effective substrate in lower intestine or colon (e.g. the products with the brand name Eudragit®L and Eudragit®S from Fa. Röhm, Darmstadt, Germany).

For preparation of orally applied phosphatidylcholine it is advantageous to use delayed released formulas to prevent absorption in proximal small intestine. Phosphatidylcholine could be packed in high volume (e.g. 0.88 ml content) capsules (e.g. made of gelatine). Those can be covered with arylpolymers, e.g. the above mentioned Eugradit®-preparations. A combination of Eudragit®S and L-preparations (e.g. Eudragit®L/S 100) guaranties a delayed release at pH >6.4, as it is present in terminal ileum. The use of Eudragit® preparations and their mixture (L-, S- and R-preparations) is established since a long period of time. In addition it is possible that also other covershield materials or application forms (also new developments) can be used for specific release of phosphatidylcholine in terminal ileum if they are proven to provide the best solution to the problem.

For preparation of clysmas phosphatidylcholine (lecithin) preparations can be solved in lipophilic solution media (e.g. soya oil). The applied dosage may for example range from 5–20 g in 100 ml soya oil. 100 ml of this solution can be applied rectally as clysma. In addition, suppositories or foam preparations can be used as application forms.

Subject of the invention are medications containing phosphatidylcholine in therapeutic effective amounts which is sufficient to achieve a mucosa protective effect in colon. The content of the effective substrate in the final preparation amounts 1–500 mg, preferentially 100–300 mg. For oral application suitable formulas are tablets, granulates, capsules, pellets or pellet tablets. The forms of medication can further contain usual pharmaceutical additions, such as supportives or carrier substances. For the rectal application primarily suitable preparations are clysmas, foam preparations, ointments, gels, lotions and suppositories. These contain the effective substrate in amounts of 10 mg–10 g, preferentially up to 5 g. According to the severity of the disease the formulas are applied once or several times daily.

Issue of the present invention is in addition a diagnostic procedure to detect diseases which are associated with reduced secretion of phosphatidylcholine in the intestinal lumen, e.g. ulcerative colitis, pouchitis (in ulcerative colitis patients) or diversion colitis. In this context, the present invention relates to a procedure to determine the phosphatidylcholine concentration in mucus of colonic mucosa, where the probe to be analyzed can be obtained by means of a dab sample of rectal mucus. Thereafter the probe will be analyzed by a suitable lipidchemical determination, e.g. by mass spectroscopy for analysis of the lipidcomposition.

It was of surprise to find that as indicator for the mucosa protective effect of phosphatidylcholine in intestine the determination of MDR3 analogous proteins is of diagnostic significance (MDR=multi drug resistance). The lack of MDR3 analogous proteins in terminal ileum can represent in this context an indicator for insufficient phosphatidylcholine secretion into the intestinal lumen with consequent change of the colonic mucus composition and increased susceptibility to local bacteria. Insufficient production of MDR3 analogous proteins thus may explain the reduced amount of phosphatidylcholine in intestinal lumen. In the sense of the presented invention, it could be shown that in mucosal epithelium of the terminal ileum or of the pouch of patients with ulcerative colitis, no MDR3-analogoos protein is present. Therefore, phosphatidylcholine secretion is significantly impaired as demonstrated by incubation experiments with biopsy probes. Accordingly, another issue of the present invention is the determination of MDR3-analogous proteins in terminal ileum and pouch for diagnosis of ulcerative colitis. This includes also all diseases associated with reduced presence of MDR3-analogous proteins.

The determination of the concentration or amount of MDR3-analogous proteins may also allow conclusions for the required optimal doses of phosphatidylcholine during the course of treatment with the invention related medications. Thus this diagnostic procedure enables an individual adaption of the required dosis of phosphatidylcholine for treatment of the patients.

Moreover, the determination of phosphatidylcholine in intestinal lumen may also allow control of therapy under the aspect of compliance of the patients.

The determination of MDR3-analogous proteins is indirectly performed by use of RT-PCR amplification of the coding RNA (genetic information).

The MDR3 protein or the MDR3-related proteins represent phospholipid transporters in plasma membranes. The human MDR (P-glycoprotein) gene family consists of two members (MDR1 and MDR3). Phylogenetically they belong to the very old super family of ABC transporters (ATP-binding-cassette). These proteins transport most diverse substrates (hydrophobic molecules, oxyanions, $Cl^-$ etc.) from inside of cells across the plasma membrane to the outside by expenditure of energy (ATP). In the genome both homologous MDR genes are positioned close to each other (MDR3 about 30 kb downstream of MDR1) and span together a distance of about 230 kb. Both genes consist of 28 exons, in MDR3 27 of these contain the coding region. Four splice variants of the MDR3 gene are known, each of which leaving the reading frame intact. In the variant $C^{-141}$ the complete exon 23 is missing, thus leading to a coding region which is shortened by 141 nucleotides. Exon 23 contains the transmembrane domain 11. A deletion could lead to a protein with completely different membrane topology. In MDR3 expressing tissues, the normal transcript and its variants are mostly present in equal abundancy.

The product of the MDR1 gene is responsible for resistance development towards different cytostatic drugs and thus gave the family the name: multidrug resistance (MDR). MDR3 is a membrane associated, 170 kD, energy dependent efflux pump for different lipophilic substances. Comparable to the other members of the ATP transporters, MDR1 consists of two homologous halves, each with 6 transmembrane domains and one nucleotide binding site.

MDR3 is identically structured, but reveals another tissue specific distribution pattern as well as another function, since it does not lead to "multidrug resistance". In mice in which the corresponding mouse specific gene (mdr2) is turned off (knock-out mouse model), a complete inability of the liver to secrete phosphatidylcholine into bile was detected. It was concluded that also MDR3 P-glycoprotein is responsible for transport of phosphatidylcholine out of liver cells into bile. About the presence of MDR3 in the remaining gastrointestinal tract nothing has been reported in the literature yet.

The following examples explain the invention in representative fashion.

EXAMPLE 1

Determination of MDR3-analogous proteins by MDR3-RNA in gastrointestinal tract using RT-PCR. For examination of possible expression, primers for amplification of MDR3-specific transcript were synthesized. Aim of the primer design is the specific and efficient amplification of the desired DNA segment. To guarantee the specificity, primer sequences are selected from areas of the MDR3-cDNA sequence in which MDR3 and MDR1 reveal little homology. In this context primers are also considered MDR3 specific which show a high homology to MDR1, but where the 3'-terminal base is different to the one of the MDR1-cDNA. To guarantee an efficient amplification of the desired DNA fragment other factors have to be considered. The primer sequence has to be selected in such a way that the primer is not able to build via intramolecular hydrogen bridging loop structures or via intermolecular bindings dimer constructs. The lengths of the oligonucleotides contain preferentially 20 to 25 base pairs. The GC-content should be in the range of 50–60%. If possible, both primers of one primer pair should be localized in different exons to avoid or to be able to recognize amplification of genomic DNA by the PCR reaction.

According to the invention primer sequences were selected which allow a reliable and specific amplification of MDR3 sequences. Examples of suitable primers specific for MDR3 are marked with arrows in the attached figure (FIG. 1, MDR1 (SEQ ID NO: 1) vs MDR3 (SEQ ID NO: 2)).

Figure Legend to FIG. 1

Homology between the cDNA-sequences of MDR1 and MDR3. The upper lane shows the MDR1-sequence, the lower lane the MDR3-sequence. Identical bases are marked by vertical lines between the sequences. Sequences from which primers can be derived are boldface typed; the orientation of primers is marked by arrows (5'→3' respectively 3'←5').

Example of a Representative, MDR3-specific PCR

As 5'-primer a 24 bp oligonucleotide of bp 2411–2435 of the cDNA in exon 20 is selected (SEQ ID NO: 11). The 3'-primer is a 33 bp oligonucleotide of bp 3180–3148 and is positioned in exon 25. The created PCR product has a length of 769 bp. With this primer pair also the splice variant $C^{-141}$ can be detected in the RNA, because here the exon 23 is missing and accordingly the created PCR product is shortened by 141 base pairs. As source material for RNA isolation, biopsies are used which are obtained by gastroscopies or colonoscopies. At that time 2 biopsies of one patient are obtained for isolation of RNA using the fast-RNA kit of Fa. Dianova. The amount of total RNA isolated by this procedure yields up to 70 µg. The isolation of poly($A^+$)RNA can be renounced because the amount of transcripts is already sufficient for a PCR detection assay.

5 µg total RNA is used for first strand cDNA synthesis. The cDNA synthesis and the PCR is performed with the ReadyToGo-system (Pharmacia) according to the recommendations of the manufacturer. 5 µg total RNA are reversibly transcribed in cDNA. The PCR is conducted with 2 of 33 µl cDNA and 10 pmol of each primer in a total volume of 25 µl. The amplification is performed as follows: First incubation for 5 min at 94° C., then 33 cycles of 2 sec at 94° C., 2 sec at 55° C. and 45 sec of 72° C. The RT-PCR products are analyzed by agarose electrophoresis. The conditions for successful detection of MDR3 are tested with liver RNA, because here a particular high abundance of transcript is present. As internal standard GAPDH is amplified to compare the amount of cDNA in the different assays. The employed method is also suitable for "light cycler"—technology (Roche Diagnostic GmbH or the "Tac Man"—PCR technology (Perkin Elmer Applied Biosystems) by which a large number of samples can simultaneously, fast, and (semi)quantitatively be determined. Biopsies of esophagus, stomach, duodenum, terminal ileum, colon transversum and rectum will be analyzed. In healthy probants MDR3 transcripts could be detected in stomach, duodenum and terminal ileum, whereas they were lacking in esophagus, colon transversum and rectum.

With the above mentioned approach the splice variant $C^{-141}$ is always and in same quantity coamplified. Both PCR products were then cloned in puc18 and sequenced. Herewith it could be documented that the amplified sequences indeed were MDR3. With the above described method it is basically also possible to detect beside the organ specific MDR3 analogous protein other homologous proteins in ileum which by way of example may represent isoforms of the MDR3 analogous protein (e.g. isoform of the liver or intestinal MDR3 protein).

EXAMPLE 2

Expression of MDR3 analogous proteins (RNA) in ileo-anal pouch epithelium. Patients were examined who received a pouch after colectomy due to a progressive ulcerative colitis. In none of these ulcerative colitis patients a MDR3 analogous transcript was detected in the pouch epithelium. Therefore the question arised whether the lack of transcripts is due to the fact that they were ulcerative colitis patients. It would be conceivable that with installation of a pouch per se and the concomitant change of the bacterial environment for the terminal ileum a changed expression may have been induced. Thus for comparison patients have been examined who received a pouch after colectomy due to familial adenomatous polyposis (FAP). These patients had MDR3 transcripts in pouch epithelium. It indicated that loss of MDR3 in pouch epithelium is specific for ulcerative colitis. The accordingly induced impaired secretion of phosphatidylcholine into the mucus could have implications for the development of the observed pouchitis. Since the pouch epithelium corresponds to the epithelium of the terminal ileum, it would be conclusive that in ulcerative colitis in this ileal segment MDR3 is also absent.

EXAMPLE 3

Expression of MDR3 analogous proteins (RNA) in terminal ileum of healthy subjects, patients with Crohn's diseases and ulcerative colitis. It was examined whether patients with ulcerative colitis reveal a MDR3 analogous expression of MDR3 in terminal ileum. 31 patients with ulcerative colitis were analyzed in comparison to 14 healthy subjects and 6 patients with Crohn's diseases. In no patient with ulcerative colitis MDR3 analogous RNA was detected in terminal ileum with the applied highly sensitive technique, whereas it was detectable in all healthy subjects as well as in patients with Crohn's disease. This clear cut result indicates that only in ulcerative colitis such a defect in the expression of the MDR3 analogon is present. From this it can be concluded that in these patients an impaired phospholipid secretion in intestine is present which disturbs the mucus composition in such a way that bacteria can more easily attack the epithelium.

What is claimed is:

1. A method of treating diseases of the colon mucosa, comprising administering a therapeutically effective amount of substrate phosphatidylcholine in a pH-dependent delayed time release preparation.

2. The method of treating diseases of the colon mucosa according to claim 1, wherein the local administration of phosphatidylcholine comprises orally administering phosphatidylcholine with pH-dependent delayed time release of the effective substrate in the distal ileum or colon.

3. The method of treating diseases of the colon mucosa according to claim 1, wherein the diseases of the colon mucosa include Colitis ulcerosa, Pouchitis, Crohn's disease, ulcerative colitis, diversion colitis, infectious enteritis/colitis, inflammations due irradiation, antibiotics, chemotherapeutic agents or chemicals, and prophylaxis of colonic cancer.

4. The method of treating diseases of the colon mucosa according to claim 1, wherein the step of administering the substrate phosphatidylcholine comprises orally administering the preparation with substrate phosphatidylcholine in a therapeutic amount of 1–500 mg w/w to the final preparation.

5. A method of treating diseases in the distal ileum comprising orally administering a pH-dependent delayed time release preparation with substrate phosphatidylcholine in a therapeutic amount of 1–500 mg w/w to the final preparation.

6. The method of treating diseases according to claim 1, wherein the pH-dependent delayed time release preparation comprises a gastric acid resistant substance.

7. The method of treating diseases according to claim 6, wherein the gastric acid resistant substance is selected from the group consisting of film covershields and carrier matrices.

8. The method of treating diseases according to claim 6, wherein the gastric acid resistant substance contains acrylpolymers.

9. Medications containing an effective substrate phosphatidylcholine in a pH-dependent delayed time release preparation and in a therapeutic concentration to treat diseases in which the mucosa protective effect of phosphatidylcholine in colon is of advantage.

10. Medications according to claim 9 for treatment of colonic diseases or colonic inflammation.

11. Medications according to claim 9 as orally applied formulas with pH-dependent delayed time release of the effective substrate in distal ileum and colon.

12. The medications according to claim 9, wherein said pH-dependent delayed time release preparation comprises a gastric acid resistant substance.

13. The medications according to claim 12, wherein said gastric acid resistant substance is selected from the group consisting of film covershields and carrier matrices.

14. The medications according to claim 13, wherein said gastric acid resistant substance contains acrylpolymers.

* * * * *